(12) United States Patent
Kim et al.

(10) Patent No.: US 10,406,204 B2
(45) Date of Patent: Sep. 10, 2019

(54) MULTIMERIC ANTIMICROBIAL PEPTIDE COMPLEX WHICH IS DISPLAYED ON CELL SURFACE

(71) Applicants: KOREA ADVANCED INSTITUTE OF SCIENCE AND TECHNOLOGY, Daejeon (KR); INTELLIGENT SYNTHETIC BIOLOGY CENTER, Daejeon (KR)

(72) Inventors: Sun-Chang Kim, Daejeon (KR); Ju Ri Shin, Daejeon (KR); Ki Jung Lim, Daejeon (KR); Da Jung Kim, Daejeon (KR); Young Woong Lee, Daejeon (KR); Su A Jang, Daejeon (KR); Bong Hyun Sung, Daejeon (KR)

(73) Assignees: KOREA ADVANCED INSTITUTE OF SCIENCE AND TECHNOLOGY, Daejeon (KR); INTELLIGENT SYNTHETIC BIOLOGY CENTER, Daejeon (KR)

(*) Notice: Subject to any disclaimer, the term of this patent is extended or adjusted under 35 U.S.C. 154(b) by 34 days.

(21) Appl. No.: 14/846,637

(22) Filed: Sep. 4, 2015

(65) Prior Publication Data
US 2015/0366992 A1 Dec. 24, 2015

Related U.S. Application Data

(62) Division of application No. 13/991,825, filed as application No. PCT/KR2010/009434 on Dec. 28, 2010, now abandoned.

(30) Foreign Application Priority Data

Dec. 6, 2010 (KR) .................. 10-2010-0123792

(51) Int. Cl.

| | |
|---|---|
| *A61K 38/16* | (2006.01) |
| *C12P 21/06* | (2006.01) |
| *C07K 14/245* | (2006.01) |
| *C07K 14/21* | (2006.01) |
| *C07K 14/47* | (2006.01) |
| *C12P 21/02* | (2006.01) |
| *C12N 15/62* | (2006.01) |
| *C07K 14/255* | (2006.01) |
| *A61K 47/65* | (2017.01) |
| *A61K 47/69* | (2017.01) |

(52) U.S. Cl.
CPC .............. *A61K 38/16* (2013.01); *A61K 47/65* (2017.08); *A61K 47/6901* (2017.08); *C07K 14/21* (2013.01); *C07K 14/245* (2013.01); *C07K 14/255* (2013.01); *C07K 14/4723* (2013.01); *C12N 15/62* (2013.01); *C12P 21/02* (2013.01); *C12P 21/06* (2013.01); *C07K 2319/035* (2013.01); *C07K 2319/50* (2013.01)

(58) Field of Classification Search
None
See application file for complete search history.

(56) References Cited

U.S. PATENT DOCUMENTS

| | | | |
|---|---|---|---|
| 6,008,195 A | * | 12/1999 | Selsted ............. A61K 38/1709 |
| | | | 514/2.7 |
| 6,713,062 B1 | | 3/2004 | Merchant |
| 7,348,402 B2 | | 3/2008 | Kim et al. |
| 2005/0191720 A1 | | 9/2005 | Sung et al. |
| 2006/0259995 A1 | | 11/2006 | Cayouette et al. |
| 2008/0170991 A1 | | 7/2008 | Shi et al. |

FOREIGN PATENT DOCUMENTS

| | | |
|---|---|---|
| KR | 10-0441402 B1 | 7/2004 |
| WO | 93/24636 A1 | 12/1993 |
| WO | 2003080652 A1 | 10/2003 |
| WO | 2004/089986 A1 | 10/2004 |
| WO | 20081017483 A2 | 2/2008 |
| WO | WO 2008/052322 * | 5/2008 |

(Continued)

OTHER PUBLICATIONS

Auvin et al (Bioorganic & Medicinal Chemistry Letters 14 (2004) 3825-3828).*
Palashoff (Determining the Specificity of Pepsin for Proteolytic Digestion, (2008). Chemistry Master's Theses. Paper 1).*
Arnusch et al (Biochemistry 2007, 46, 13437-13442).*
Solomkin et al. (Clinical Infectious Diseases 2010; 50:133-64).*
Torres et al. (Infection and Immunity, May 2006, p. 2676-2685).*
GenBank ACO48685.1 (downloaded on Aug. 25, 2017 from URL:< https://www.ncbi.nlm.nih.gov/protein/226344125?report=genbank &log$=protalign&blast_rank=3&RID=UOWBYBS7014).*

(Continued)

*Primary Examiner* — Sergio Coffa
(74) *Attorney, Agent, or Firm* — Gavrilovich, Dodd & Lindsey LLP

(57) ABSTRACT

The present invention provides an antimicrobial peptide polymer comprising at least one monomer which is digested by pepsin, a multimeric antimicrobial peptide complex comprising the polymer and a cell surface anchoring motif linked to the polymer, an antimicrobial microorganism displaying the multimeric antimicrobial peptide complex, an antimicrobial composition comprising the same, a method of treating an infectious disease caused by bacteria, yeast or fungi by administering the antimicrobial composition, and a method for producing the antimicrobial microorganism. According to the invention, living microorganisms displaying an antimicrobial peptide on the cell surface thereof may be administered in vivo without having to lyse the microbial cell and isolate and purify the antimicrobial peptide, so that the antimicrobial peptide exhibits antimicrobial activity. Thus, the antimicrobial peptide may be produced at significantly reduced costs so that it may have widespread use.

7 Claims, 7 Drawing Sheets
Specification includes a Sequence Listing.

(56) References Cited

FOREIGN PATENT DOCUMENTS

WO    20091108406 A2    9/2009
WO    2010/114797 A1    10/2010

OTHER PUBLICATIONS

Sonnerat, Isabelle, First Office Action, European Patent Application No. 10860601.3, European Patent Office, dated Oct. 28, 2015.

Hamuro et al., "Specificity of immobilized porcine pepsin in H/D exchange compatible conditions," Rapid Communications In Mass Spectrometry, 2008, pp. 1041-1046, vol. 22.

Ingham, Aaron B. et al., "Recombinant production of antimicrobial peptides in heterologous microbial systems", Biotechnology and Applied Biochemistry, vol. 47, No. 1, May 1, 2007, pp. 1-9.

Lee, S. Y. et al., "Microbial cell-surface display", Trends in Biotechnology, Elsevier Publications, Cambridge, GB, vol. 21, No. 1, Jan. 1, 2003, pp. 45-52.

Shin, Ju Ri et al., "Display of Multimeric Antimicrobial Peptides on the *Escherichia coli* Cell Surface and Its Application as Whole-Cell Antibiotics", PLOS ONE, vol. 8, No. 3, Mar. 2013, e58997, pp. 1-10.

Sonnerat, Isabelle, Supplementary European Search Report, EP 10 86 0601, European Patent Office, dated Apr. 23, 2014.

Office Action, State Intellectual Property Office of P.R.C., Chinese Patent Application No. 201080071168.1, dated May 5, 2016.

* cited by examiner

SEQUENCE LISTING

```
<160> NUMBER OF SEQ ID NOS: 30

<210> SEQ ID NO 1
<211> LENGTH: 58
<212> TYPE: DNA
<213> ORGANISM: Artificial Sequence
<220> FEATURE:
<223> OTHER INFORMATION: primer for Hinge2L

<400> SEQUENCE: 1 gaagacccccg tgttgttcgt cagtggccga ttggtcgtgt cgttcgccgt gttgttcg       58

<210> SEQ ID NO 2
<211> LENGTH: 57
<212> TYPE: DNA
<213> ORGANISM: Artificial Sequence
<220> FEATURE:
<223> OTHER INFORMATION: primer for Hinge2L

<400> SEQUENCE: 2
ggatggatcc taagcacgca gacgaacgac gcgacgaaca acacggcgaa cgacacg         57

<210> SEQ ID NO 3
<211> LENGTH: 51
<212> TYPE: DNA
<213> ORGANISM: Artificial Sequence
<220> FEATURE:
<223> OTHER INFORMATION: primer for Lpp-OmpA

<400> SEQUENCE: 3
```
cgccatatga agctactaa actggtactg gcaacaaca atggcccgac c         51

<210> SEQ ID NO 4
<211> LENGTH: 24
<212> TYPE: DNA
<213> ORGANISM: Artificial Sequence
<220> FEATURE:
<223> OTHER INFORMATION: primer for Lpp-OmpA

<400> SEQUENCE: 4
gcaaacaccg gagaaacgcc ggtg                                     24

<210> SEQ ID NO 5
<211> LENGTH: 26
<212> TYPE: DNA
<213> ORGANISM: Artificial Sequence
<220> FEATURE:
<223> OTHER INFORMATION: primer for Lpp-OmpA

<400> SEQUENCE: 5
ttctccggtg tttgctggcg gtgttg                                   26

<210> SEQ ID NO 6
<211> LENGTH: 51
<212> TYPE: DNA
<213> ORGANISM: Artificial Sequence
<220> FEATURE:
<223> OTHER INFORMATION: primer for Lpp-OmpA

<400> SEQUENCE: 6
cgggatccta gtgatggtga tggtgatgaa cacgcagtct tccacgggta g        51

<210> SEQ ID NO 7
<211> LENGTH: 369
<212> TYPE: DNA
<213> ORGANISM: Artificial Sequence
<220> FEATURE:
<223> OTHER INFORMATION: DNA sequence of Lpp-OmpA

<400> SEQUENCE: 7
atgaaagcta ctaaactggt actgggcaac aacaatggcc cgacccatga aaaccaactg   60
ggcgctggtg cttttggtgg ttaccaggtt aacccgtatg ttggctttga atgggttac   120 gactggttag gtcgtatgcc gtacaaaggc agcgttgaaa acgttgcata caaagctcag  180
ggcgttcaac tgaccgctaa actgggttac ccaatcactg acgacctgga catctacact  240
cgtctgggtg gcatggtatg gcgtgcagac actaaatcca acgtttatgg taaaaaccac  300
gacaccggcg tttctccggt gtttgctggc ggtgttgagt acgcgatcac tcctgaaatc  360
gctacccgt                                                          369

<210> SEQ ID NO 8
<211> LENGTH: 123
<212> TYPE: PRT
<213> ORGANISM: Artificial Sequence
<220> FEATURE:
<223> OTHER INFORMATION: amion acid sequence of Lpp-OmpA

<400> SEQUENCE: 8

Met Lys Ala Thr Lys Leu Val Leu Gly Asn Asn Asn Gly Pro Thr His
1               5                   10                  15

Glu Asn Gln Leu Gly Ala Gly Ala Phe Gly Gly Tyr Gln Val Asn Pro
            20                  25                  30

Tyr Val Gly Phe Glu Met Gly Tyr Asp Trp Leu Gly Arg Met Pro Tyr

```
                35                  40                  45
Lys Gly Ser Val Glu Asn Gly Ala Tyr Lys Ala Gln Gly Val Gln Leu
         50                  55                  60

Thr Ala Lys Leu Gly Tyr Pro Ile Thr Asp Asp Leu Asp Ile Tyr Thr
 65                  70                  75                  80

Arg Leu Gly Gly Met Val Trp Arg Ala Asp Thr Lys Ser Asn Val Tyr
                 85                  90                  95

Gly Lys Asn His Asp Thr Gly Val Ser Pro Val Phe Ala Gly Gly Val
            100                 105                 110

Glu Tyr Ala Ile Thr Pro Glu Ile Ala Thr Arg
        115                 120

<210> SEQ ID NO 9
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 9

Arg Val Val Arg Gln Trp Pro Ile Gly Arg Val Val Arg Arg Val Val
1               5                   10                  15

Arg Arg Val Val Arg
            20

<210> SEQ ID NO 10
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 10

Lys Val Val Lys Gln Trp Pro Ile Gly Lys Val Val Lys Lys Val Val
1               5                   10                  15

Lys Lys Val Val Lys
            20

<210> SEQ ID NO 11
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 11

Arg Val Val Lys Gln Trp Pro Ile Gly Arg Val Val Lys Arg Val Val
1               5                   10                  15

Lys Arg Val Val Lys
            20

<210> SEQ ID NO 12
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 12

Lys Val Val Arg Gln Trp Pro Ile Gly Lys Val Val Arg Lys Val Val
1               5                   10                  15

Arg Lys Val Val Arg
```

20

<210> SEQ ID NO 13
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 13

Arg Val Val Arg Asn Trp Pro Ile Gly Arg Val Val Arg Val Val
1               5                   10                  15

Arg Arg Val Val Arg
            20

<210> SEQ ID NO 14
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 14

Lys Val Val Lys Asn Trp Pro Ile Gly Lys Val Val Lys Lys Val Val
1               5                   10                  15

Lys Lys Val Val Lys
            20

<210> SEQ ID NO 15
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 15

Arg Val Val Lys Asn Trp Pro Ile Gly Arg Val Val Lys Arg Val Val
1               5                   10                  15

Lys Arg Val Val Lys
            20

<210> SEQ ID NO 16
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 16

Lys Val Val Arg Asn Trp Pro Ile Gly Lys Val Val Arg Lys Val Val
1               5                   10                  15

Arg Lys Val Val Arg
            20

<210> SEQ ID NO 17
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 17

Arg Val Val Arg Arg Val Val Arg Arg Val Val Arg Gln Trp Pro Ile
1               5                   10                  15

```
Gly Arg Val Val Arg
        20

<210> SEQ ID NO 18
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 18

Lys Val Val Lys Lys Val Val Lys Lys Val Val Lys Gln Trp Pro Ile
1               5                   10                  15

Gly Lys Val Val Lys
        20

<210> SEQ ID NO 19
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 19

Arg Val Val Lys Arg Val Val Lys Arg Val Val Lys Gln Trp Pro Ile
1               5                   10                  15

Gly Arg Val Val Lys
        20

<210> SEQ ID NO 20
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 20

Lys Val Val Arg Lys Val Val Arg Lys Val Val Arg Gln Trp Pro Ile
1               5                   10                  15

Gly Lys Val Val Arg
        20

<210> SEQ ID NO 21
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 21

Arg Val Val Arg Arg Val Val Arg Arg Val Val Arg Asn Trp Pro Ile
1               5                   10                  15

Gly Arg Val Val Arg
        20

<210> SEQ ID NO 22
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 22

Lys Val Val Lys Lys Val Val Lys Lys Val Val Lys Asn Trp Pro Ile
1               5                   10                  15
```

Gly Lys Val Val Lys
        20

<210> SEQ ID NO 23
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 23

Arg Val Val Lys Arg Val Val Lys Arg Val Val Lys Asn Trp Pro Ile
1               5                   10                  15

Gly Arg Val Val Lys
        20

<210> SEQ ID NO 24
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 24

Lys Val Val Arg Lys Val Val Arg Lys Val Val Arg Asn Trp Pro Ile
1               5                   10                  15

Gly Lys Val Val Arg
        20

<210> SEQ ID NO 25
<211> LENGTH: 510
<212> TYPE: DNA
<213> ORGANISM: Artificial Sequence
<220> FEATURE:
<223> OTHER INFORMATION: DNA sequence of Lpp-OmpA-Hinge2L2

<400> SEQUENCE: 25

```
atgaaagcta ctaaactggt actgggcaac aacaatggcc cgacccatga aaaccaactg      60
ggcgctggtg cttttggtgg ttaccaggtt aacccgtatg ttggctttga atgggttac     120
gactggttag gtcgtatgcc gtacaaaggc agcgttgaaa acggtgcata caaagctcag     180
ggcgttcaac tgaccgctaa actgggttac ccaatcactg acgacctgga catctacact     240
cgtctgggtg gcatggtatg gcgtgcagac actaaatcca acgtttatgg taaaaaccac     300
gacaccggcg tttctccggt gtttgctggc ggtgttgagt acgcgatcac tcctgaaatc     360
gctacccgtg aagactgcg tgttgttcgt cagtggccga ttggtcgtgt cgttcgccgt     420
gttgttcgtc gcgtcgttcg tctgcgtgtt gttcgtcagt ggccgattgg tcgtgtcgtt     480
cgccgtgttg ttcgtcgcgt cgttcgtctg                                     510
```

<210> SEQ ID NO 26
<211> LENGTH: 576
<212> TYPE: DNA
<213> ORGANISM: Artificial Sequence
<220> FEATURE:
<223> OTHER INFORMATION: DNA sequence of Lpp-OmpA-Hinge2L3

<400> SEQUENCE: 26

```
atgaaagcta ctaaactggt actgggcaac aacaatggcc cgacccatga aaaccaactg      60
ggcgctggtg cttttggtgg ttaccaggtt aacccgtatg ttggctttga atgggttac     120
gactggttag gtcgtatgcc gtacaaaggc agcgttgaaa acggtgcata caaagctcag     180
```

```
ggcgttcaac tgaccgctaa actgggttac ccaatcactg acgacctgga catctacact      240
cgtctgggtg gcatggtatg gcgtgcagac actaaatcca acgtttatgg taaaaaccac      300
gacaccggcg tttctccggt gtttgctggc ggtgttgagt acgcgatcac tcctgaaatc      360
gctacccgtg aagactgcg tgttgttcgt cagtggccga ttggtcgtgt cgttcgccgt       420
gttgttcgtc gcgtcgttcg tctgcgtgtt gttcgtcagt ggccgattgg tcgtgtcgtt      480
cgccgtgttt tcgtcgcgt cgttcgtctg cgtgttgttc gtcagtggcc gattggtcgt       540
gtcgttcgcc gtgttgttcg tcgcgtcgtt cgtctg                                576
```

```
<210> SEQ ID NO 27
<211> LENGTH: 642
<212> TYPE: DNA
<213> ORGANISM: Artificial Sequence
<220> FEATURE:
<223> OTHER INFORMATION: DNA sequence of Lpp-OmpA-Hinge2L4

<400> SEQUENCE: 27
atgaaagcta ctaaactggt actgggcaac aacaatggcc cgacccatga aaaccaactg      60
ggcgctggtg cttttggtgg ttaccaggtt aacccgtatg ttggctttga atgggttac       120 gactggttag gtcgtatgcc gtacaaaggc agcgttgaaa acggtgcata caaagctcag      180
ggcgttcaac tgaccgctaa actgggttac ccaatcactg acgacctgga catctacact      240
cgtctgggtg gcatggtatg gcgtgcagac actaaatcca acgtttatgg taaaaaccac      300
gacaccggcg tttctccggt gtttgctggc ggtgttgagt acgcgatcac tcctgaaatc      360
gctacccgtg aagactgcg tgttgttcgt cagtggccga ttggtcgtgt cgttcgccgt       420
gttgttcgtc gcgtcgttcg tctgcgtgtt gttcgtcagt ggccgattgg tcgtgtcgtt      480
cgccgtgttt tcgtcgcgt cgttcgtctg cgtgttgttc gtcagtggcc gattggtcgt       540
gtcgttcgcc gtgttgttcg tcgcgtcgtt cgtctgcgtg ttgttcgtca gtggccgatt      600
ggtcgtgtcg ttcgccgtgt tgttcgtcgc gtcgttcgtc tg                         642
```

```
<210> SEQ ID NO 28
<211> LENGTH: 132
<212> TYPE: DNA
<213> ORGANISM: Artificial Sequence
<220> FEATURE:
<223> OTHER INFORMATION: DNA sequence of Hinge2L2

<400> SEQUENCE: 28
cgtgttgttc gtcagtggcc gattggtcgt gtcgttcgcc gtgttgttcg tcgcgtcgtt      60
cgtctgcgtg ttgttcgtca gtggccgatt ggtcgtgtcg ttcgccgtgt tgttcgtcgc      120
gtcgttcgtc tg                                                          132
```

```
<210> SEQ ID NO 29
<211> LENGTH: 198
<212> TYPE: DNA
<213> ORGANISM: Artificial Sequence
<220> FEATURE:
<223> OTHER INFORMATION: DNA sequence of Hinge2L3

<400> SEQUENCE: 29
cgtgttgttc gtcagtggcc gattggtcgt gtcgttcgcc gtgttgttcg tcgcgtcgtt      60
cgtctgcgtg ttgttcgtca gtggccgatt ggtcgtgtcg ttcgccgtgt tgttcgtcgc      120
gtcgttcgtc tgcgtgttgt tcgtcagtgg ccgattggtc gtgtcgttcg ccgtgttgtt     180
```

```
<210> SEQ ID NO 30
<211> LENGTH: 264
<212> TYPE: DNA
<213> ORGANISM: Artificial Sequence
<220> FEATURE:
<223> OTHER INFORMATION: DNA sequence of Hinge2L4

<400> SEQUENCE: 30
cgtgttgttc gtcagtggcc gattggtcgt gtcgttcgcc gtgttgttcg tcgcgtcgtt      60
cgtctgcgtg ttgttcgtca gtggccgatt ggtcgtgtcg ttcgccgtgt tgttcgtcgc     120
gtcgttcgtc tgcgtgttgt tcgtcagtgg ccgattggtc gtgtcgttcg ccgtgttgtt     180
cgtcgcgtcg ttcgtctgcg tgttgttcgt cagtggccga ttggtcgtgt cgttcgccgt     240
gttgttcgtc gcgtcgttcg tctg                                             264
```

MULTIMERIC ANTIMICROBIAL PEPTIDE COMPLEX WHICH IS DISPLAYED ON CELL SURFACE

CROSS REFERENCE TO RELATED APPLICATIONS

This application is a divisional of U.S. application Ser. No. 13/991,825, filed Sep. 10, 2013, which is a U.S. National Stage Application filed under 35 U.S.C. § 371 and claims priority to International Application No. PCT/KR2010/009434, filed Dec. 28, 2010, which application claims priority under 35 U.S.C. § 119 to Korean Application No. 10-2010-0123792, filed Dec. 6, 2010, the disclosures of which are incorporated herein by reference.

TECHNICAL FIELD

The present invention relates to an antimicrobial peptide polymer comprising at least one monomer which is digested by pepsin, a multimeric antimicrobial peptide complex comprising the polymer and a cell surface anchoring motif linked to the polymer, an antimicrobial microorganism displaying the multimeric antimicrobial peptide complex, an antimicrobial composition comprising the same, a method of treating an infectious disease caused by bacteria, yeast or fungi by administering the antimicrobial composition, and a method for producing the antimicrobial microorganism.

BACKGROUND ART

To protect humans from pathogenic microorganisms, many antibiotics have been discovered, developed and used. However, the misuse of antibiotics has resulted in a rapid increase in antibiotic-resistant strains, and thus the number of usable antibiotics has been limited. For this reason, there has been a demand for novel substances which have activation mechanisms different from conventional antibiotics, exhibit activity against antibiotic-resistant microorganisms, do not cause problems on resistance and do not remain in vivo for a long period of time. Typical candidates capable of satisfying this demand include antimicrobial peptides.

Unlike conventional antibiotics, antimicrobial peptides have potent antimicrobial activities against a wide range of microorganisms, are physically and chemically stable in heat, acid or alkali and consist of a small number of amino acids (5-50 amino acids). Thus, these antimicrobial peptides have advantages in that they are easily degraded after antimicrobial action so that they do not remain in vivo, indicating that they do not cause toxicity in vivo. Thus, the antimicrobial peptides can be used as next-generation antibiotic substances and are highly applicable in industrial fields, including the pharmaceutical and food fields.

The present inventors previously developed antimicrobial peptides having potent antimicrobial activity against a wide range of microorganisms (Korean Patent Registration No. 0441402).

For industrial application of these antimicrobial peptides, methods capable of producing large amounts of the antimicrobial peptides in a cost-effective manner are by necessity required, but conventional methods for producing the antimicrobial peptides cannot provide large amounts of the antimicrobial peptides in a cost-effective manner. In other words, the use of a chemical synthesis method, which is a conventional method for peptide production has low economic efficiency, and when an antimicrobial peptide is produced from microorganisms using genetic engineering technology there are problems in that the antimicrobial peptide is expressed at a low level and shows antimicrobial activity against the host and in that the expressed antimicrobial peptide is easily degraded by proteinases in the host.

In addition, in order to highly express an antimicrobial peptide in microorganisms, a method of producing a desired peptide from host microorganisms using a fusion partner without killing the host cells was generally used in the prior art.

In the above method, in order to recover the antimicrobial peptide, it is required to lyse the host cell to obtain an insoluble fusion protein, digest the fusion protein and isolate and purify the antimicrobial peptide using a chromatography or ion-exchange column. However, the above method has a critical problem in that a large amount of the antimicrobial peptide is lost during the recovery process so that the yield thereof is significantly reduced, resulting in a significant increase in the price of the antimicrobial peptide.

To overcome this problem, an attempt was made to fuse a cell surface display protein with an antimicrobial peptide to display the antimicrobial peptide on the cell surface. As a result, the cell lysis process could be omitted by displaying the antimicrobial peptide on the cell surface, but there were still problems in that the cell surface display protein must be treated with a separate enzyme in order to isolate the antimicrobial peptide and in that a chromatography or ion-exchange column must be used to remove impurities.

In addition, there is a method in which an antimicrobial peptide displayed on the cell surface is used without any treatment in order to omit the process of isolating and purifying the antimicrobial peptide. However, this method has a serious problem in that the antimicrobial activity of the antimicrobial peptide attached to the cell surface is significantly reduced.

DISCLOSURE

Technical Problem

Accordingly, the present inventors have made extensive efforts to develop an antimicrobial peptide which exhibits antimicrobial activity in vivo, using living microorganisms expressing the same, without isolating and purifying the antimicrobial peptide. As a result, the present inventors have found that, when a multimeric antimicrobial peptide complex comprising a monomer which is digested by pepsin is displayed on the cell surface of *E. coli*, the displayed antimicrobial peptide exhibits antimicrobial activity in vivo without having to isolate and purify the antimicrobial peptide from the *E. coli* cells, thereby completing the present invention.

Technical Solution

In order to accomplish the above objects, the present invention provides a multimeric antimicrobial peptide complex comprising an antimicrobial peptide polymer comprising at least one monomer which is digested by pepsin, and a cell surface anchoring motif linked to the polymer.

Another object of the present invention is to provide an antimicrobial peptide polymer comprising at least one monomer which is digested by pepsin.

Still another object of the present invention is to provide a polynucleotide encoding the above multimeric antimicrobial peptide complex or polymer.

Still another object of the present invention is to provide a recombinant vector comprising the above polynucleotide.

Still another object of the present invention is to provide an antimicrobial microorganism displaying the multimeric antimicrobial peptide complex on the cell surface thereof.

Still another object of the present invention is to provide an antimicrobial pharmaceutical composition and an antimicrobial over-the-counter (OTC) drug composition, which comprise, as an active ingredient, the above multimeric antimicrobial peptide complex or antimicrobial peptide polymer or an antimicrobial microorganism displaying the above multimeric antimicrobial peptide complex on the cell surface thereof.

Still another object of the present invention is to provide a method for producing an antimicrobial microorganism displaying the above multimeric antimicrobial peptide complex on the cell surface thereof.

Yet another object of the present invention is to provide a method for treating an infectious disease caused by bacteria, yeast or fungi, the method comprising administering the antimicrobial pharmaceutical composition.

Advantageous Effects

According to the present invention, an antimicrobial peptide is produced so that it can show antimicrobial activity when living microorganisms displaying the antimicrobial peptide on the cell surface thereof are administered in vivo without having to lyse cells and isolate and purify the antimicrobial peptide. Thus, the antimicrobial peptide can be produced at significantly reduced cost so that it can have widespread use. In addition, the multimeric antimicrobial peptide complex or antimicrobial peptide polymer of the present invention is digested by the enzyme pepsin in vivo so that it is separated into monomeric antimicrobial peptide units, and the separated monomeric antimicrobial peptide units have high antimicrobial activity. Thus, the multimeric antimicrobial peptide complex or antimicrobial peptide polymer of the present invention can be effectively used for the treatment of an infectious disease caused by pathogenic bacteria, yeast or fungi, and as a substitute for conventional antibiotics.

BEST MODE

To achieve the above-described objects, in one aspect, the present invention provides a multimeric antimicrobial peptide complex comprising an antimicrobial peptide polymer and a cell surface anchoring motif linked to the polymer, wherein the antimicrobial peptide polymer comprises at least one monomer represented by the following formula 1 or 2:

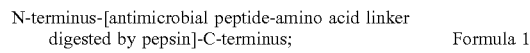

N-terminus-[antimicrobial peptide-amino acid linker digested by pepsin]-C-terminus;   Formula 1 and

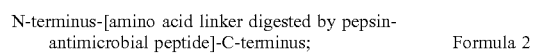

N-terminus-[amino acid linker digested by pepsin-antimicrobial peptide]-C-terminus;   Formula 2 wherein the antimicrobial peptide does not comprise the amino acid used in the linker.

In another aspect, the present invention provides an antimicrobial peptide polymer comprising at least one monomer represented by formula 1 or 2.

As used herein, the term "antimicrobial peptide polymer" refers to a polymer in which one or more monomers which are digested by pepsin are repeatedly linked by the amino acid linker that is digested by pepsin, and the term "multimeric antimicrobial peptide complex" refers to a multimeric peptide complex which comprises a cell surface anchoring motif linked to the antimicrobial peptide polymer so that it can be displayed on the cell surface of a microorganism when being expressed in the microorganism.

Figure 1:
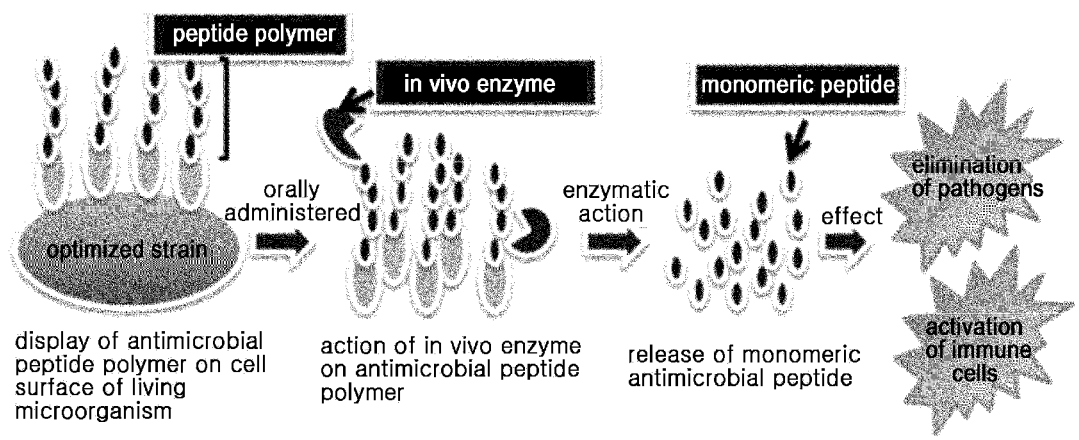
FIG. 1 shows the principle of activation of antimicrobial microorganisms that display a multimeric antimicrobial peptide complex of the present invention on the cell surface thereof.

As shown in FIG. 1, the multimeric antibacterial peptide complex of the present invention is separated into monomeric antimicrobial peptide units having antimicrobial activity, because the amino acid linker that is digested by pepsin in the monomeric antimicrobial peptide is digested by the digestive enzyme pepsin in vivo. Thus, when living microorganisms that display the multimeric antibacterial peptide are injected in vivo without isolating or purifying the multimeric antibacterial peptide from the microorganisms, effects such as the elimination of pathogens and the activation of immune cells can be induced directly in vivo by the antimicrobial activity of the antimicrobial peptide.

In the present invention, the monomer has an amino acid linker that is digested by pepsin linked to the N-terminus or C-terminus of the antimicrobial peptide.

The antimicrobial peptide is a peptide or its derivative, which penetrates microbial cells to exhibit potent antimicrobial activity against a wide range of microorganisms, including bacteria or fungi, and does not include the amino acid sequence of the amino acid linker that is digested by pepsin in order to prevent the antimicrobial peptide from being digested by pepsin.

In addition, the antimicrobial peptide may be a peptide having antimicrobial activity or its derivative. Preferably, it may be an antimicrobial peptide or its derivative, which does not include the amino acid sequence of the amino acid linker that is digested by pepsin, among antimicrobial peptides disclosed in Korean Patent Registration No. 0441402. More preferably, it may be an antimicrobial peptide having any one amino acid sequence selected from among the amino acid sequences of SEQ ID NOS: 9 to 24, or a derivative thereof. Even more preferably, it may be an antimicrobial peptide having the amino acid sequence of SEQ ID NO: 9, or a derivative thereof.

The amino acid linker that is digested by pepsin consists of one or more amino acids. Thus, it acts as a linker that links antimicrobial peptides to each other by peptide linkage, and is digested by the enzyme pepsin in vivo so that the multimeric antimicrobial peptide complex is separated into monomeric antimicrobial peptide units. The multimeric antimicrobial peptide complex or antimicrobial peptide polymer of the present invention may include one or more monomers represented by formula 1 or 2. The number of the monomers that may be included in a transformed microorganism or a vector is not limited, but is preferably 1-4.

In the present invention, both ends of the amino acid linker that is digested by pepsin are linked to the end of the antimicrobial peptide by peptide linkage. The amino acid linker consists of an amino acid sequence that enables the peptide linkage formed between the ends of the linker and N-terminus of the antimicrobial peptide to be broken by the action of the digestive enzyme pepsin.

Preferably, the amino acid linker that is digested by pepsin may consist of one or more amino acids selected from the group consisting of leucine (Leu), phenylalanine (Phe) and tyrosine (Tyr). For example, it may consist of one or more leucines, one or more phenylalanines, one or more tyrosines, or a combination thereof comprising one or more amino acids. Preferably, it may consist of one leucine, one phenylalanine or one tyrosine.

In one Example of the present invention, the pepsin-digested site of an antimicrobial peptide polymer linked to the C-terminus of an antimicrobial peptide by any amino acid linker was predicted using a computer program. As a result, it was shown that a peptide linkage formed between the end of one leucine, phenylalanine or tyrosine of the amino acid linker and the N-terminus of the antimicrobial peptide was broken while the antimicrobial peptide polymer could be separated into monomeric antimicrobial monomer units (Example 1).

In the present invention, the cell surface anchoring motif is linked to the antimicrobial peptide polymer so that the multimeric antimicrobial peptide complex is displayed on the cell surface of microorganisms.

The cell surface anchoring motif may be selected from the group consisting of outer membrane proteins, lipoproteins, autotransporters, and S-layer of surface appendage. Preferably, it may be an outer membrane protein. More preferably, it may be an outer membrane protein selected from the group consisting of an *E. coli* outer membrane protein OmpA, an *E. coli* outer membrane protein OmpA linked to the leader sequence of *E. coli* lipoprotein, an *E. coli* outer membrane protein OmpS, an *E. coli* outer membrane protein LamB, an *E. coli* outer membrane protein PhoE, an *E. coli* outer membrane protein OmpC, an *E. coli* outer membrane protein FadL, a *Salmonella* outer membrane protein OmpC, and a *Pseudomonas* outer membrane protein OprF. Even more preferably, it may be a cell surface anchoring motif (Lpp-OmpA) of SEQ ID NO: 8 which consists of *E. coli* outer membrane protein OmpA linked to the leader sequence of *E. coli* lipoprotein.

In the Examples of the present invention, antimicrobial peptide polymers $Hinge2L_1$, $Hinge2L_2$, $Hinge2L_3$ and $Hinge2L_4$, each consisting of a monomeric antimicrobial peptide (Hinge2L) having one leucine as an amino acid linker that is digested by pepsin added to the C-terminus of an antimicrobial peptide, were constructed (Example 2), and multimeric antimicrobial peptide complexes $Lpp-OmpA-Hinge2L_1$, $Lpp-OmpA-Hinge2L_2$, $Lpp-OmpA-Hinge2L_3$ and $Lpp-OmpA-Hinge2L_4$, each consisting of a cell surface anchoring motif (Lpp-OmpA), having an amino acid sequence of SEQ ID NO: 8, connected to the N-terminus of an antimicrobial peptide polymer, were constructed (Example 3).

In another aspect, the present invention provides a polynucleotide, which encodes the multimeric antimicrobial peptide complex or antimicrobial peptide polymer of the present invention, and a recombinant vector comprising the same.

In the present invention, the polynucleotide that encodes the multimeric antimicrobial peptide complex or the antimicrobial peptide polymer is a DNA (deoxyribonucleic acid) or RNA (ribonucleic acid) strand which is a nucleotide polymer consisting of nucleotide monomer units covalently bonded to each other.

The polynucleotide encoding the multimeric antimicrobial peptide complex may be a polynucleotide having any one of the nucleotide sequences of SEQ ID NO: 25 ($Lpp-OmpA-Hinge2L_2$), SEQ ID NO: 26 ($Lpp-OmpA-Hinge2L_3$) and SEQ ID NO: 27 ($Lpp-OmpA-Hinge2L_4$).

In addition, the polynucleotide encoding the antimicrobial peptide polymer may be a polynucleotide having any one of the nucleotide sequences of SEQ ID NO: 28 ($Hinge2L_2$), SEQ ID NO: 29 ($Hinge2L_3$) and SEQ ID NO: 30 ($Hinge2L_4$).

In the present invention, the recombinant vector is a means used to introduce a DNA into a microbial host cell to produce a microorganism that displays the multimeric antimicrobial peptide complex or antimicrobial peptide polymer of the present invention on the cells surface thereof. The recombinant vector that is used in the present invention can be prepared by using a known expression vector, such as a plasmid vector, a cosmid vector or a bacteriophage vector. The vector can be easily prepared by those skilled in the art according to a known method using DNA recombination technology.

The recombinant vector that is used in the present invention may be a pGEM T-easy vector or a pET21c vector, and preferably a pET21c vector.

The recombinant vector of the present invention is a recombinant vector to which a polynucleotide encoding the multimeric antimicrobial peptide complex or antimicrobial peptide polymer of the present invention is operably linked. As used herein, the term "operably linked" means that an expression control sequence is linked so as to control the transcription and translation of a polynucleotide sequence encoding the multimeric antimicrobial peptide complex or antimicrobial peptide polymer of the present invention. Specifically, it means that a reading frame is accurately maintained so that the polynucleotide sequence is expressed under the control of the expression control sequence (including a promoter) to produce the multimeric antimicrobial peptide complex or antimicrobial peptide polymer that is encoded by the polynucleotide sequence.

In still another aspect, the present invention provides an antimicrobial microorganism transformed with the recombinant vector to display the multimeric antimicrobial peptide complex on the cell surface thereof.

As used herein, the term "antimicrobial microorganism" refers to a microorganism capable of displaying an antimicrobial peptide on the cell surface thereof. The antimicrobial microorganism of the present invention functions to display the multimeric antimicrobial peptide complex, which can be cleaved into monomeric antimicrobial peptides by the digestive enzyme pepsin in the cells, on the cell surface, so that the antimicrobial microorganism itself kills pathogens in vivo. Thus, the antimicrobial microorganism of the present invention can be used as a substitute for antibiotics.

As used herein, the term "transformation" means that a gene is introduced into a host cell so that it can be expressed in the host cell. As the transformed gene, any gene which is inserted in the chromosome of a host cell or located outside the chromosome may be used without limitation, as long as it can be expressed in the host cell.

In addition, the gene is a polynucleotide capable of encoding the polypeptide, and examples thereof include DNA and RNA. The gene may be introduced in any form, as long as it can be introduced and expressed in a host cell. For example, the gene may be introduced into a host cell in the form of an expression cassette that is a polynucleotide structure including all elements required for self-expression. The expression cassette generally includes a promoter operably linked to the gene, a transcription termination signal, a ribosome binding site and a translation termination signal. The expression cassette may be in the form of a self-replicable expression vector. In addition, the gene itself may be introduced into a host cell, or the gene may be introduced into a host cell in the form of a polynucleotide structure and may be operably linked to a sequence required for expression in the host cell.

The antimicrobial microorganism is a microorganism transformed with the recombinant vector, which comprises the polynucleotide encoding the multimeric antimicrobial peptide complex, so as to be able to display the multimeric antimicrobial peptide complex on the cell surface thereof. Examples of the antimicrobial microorganism include *Escherichia* sp., *Bacilus* sp., *Aerobacter* sp., *Serratia* sp., *Providencia* sp., *Erwinia* sp., *Schizosaccharomyces* sp., *Enterobacteria* sp., *Zygosaccharomyces* sp., *Leptospira* sp. *Deinococcus* sp., *Pichia* sp., *Kluyveromyces* sp. *Candida* sp., *Hansenula* sp., *Debaryomyces* sp., *Mucor* sp., *Torulopsis* sp., *Methylobacter* sp., *Salmonella* sp., *Bacillus* sp., *Streptomyces* sp., *Pseudomonas* sp., *Brevibacterium* sp., and *Corynebacterium* sp. microorganisms.

Preferably, the antimicrobial microorganism may be an *Escherichia* sp. microorganism, more preferably *E. coli*, and even more preferably *E. coli*. BL21 (DE3).

In the Examples of the present invention, it was shown that an *E. coli* strain transformed with a recombinant vector comprising a polynucleotide encoding the multimeric antimicrobial peptide complex was constructed (Example 4), and the expression of the multimeric antimicrobial peptide complex in the transformed *E. coli* cells was induced by IPTG, after which whether the multimeric antimicrobial peptide complex was displayed on the cell surface. As a result, it could be seen that the monomer, dimer and trimer of the antimicrobial peptide Hinge2L linked to the cell surface anchoring motif were displayed on the cell surface of the *E. coli* strain (Examples 5 and 6).

In another aspect, the present invention provides an antimicrobial pharmaceutical composition comprising, as an active ingredient, the multimeric antimicrobial peptide complex, antimicrobial peptide polymer or antimicrobial microorganism of the present invention.

In still another aspect, the present invention provides a method for treating an infectious disease caused by pathogenic bacteria, yeast or fungi, the method comprising administering the above antimicrobial pharmaceutical composition to a subject having the infectious disease.

In the present invention, pathogenic bacteria refers to any microorganisms, which invade living animals or plants and is parasitic thereon to cause a disease or harm to the animals or plants. Examples of the pathogenic bacteria include gram-positive bacteria and gram-negative bacteria. Preferably, the pathogenic bacteria may be gram-positive *Staphylococus aureus* or gram-negative *Escherichia coli*.

In addition, examples of the pathogenic yeast and fungi include, but are not limited to, *Candida albicans, Aspergillus humigatus, Saccharomyces cerevisiae* and *Cryptococcus neoformans*.

In the present invention, the infectious disease caused by pathogenic bacteria may be cholera caused by *Vibrio cholera*; bacillary dysentery caused by dysentery *bacillus*; pertussis caused by *Bordetella pertussis*; typhoid fever caused by *Salmonella typhi*; laryngeal diphtheria and nasal diphtheria caused by *Corynebacterium diphtheria*; bubonic plague and pneumonic plaque caused by *Yersinea pestis*; scarlet fever, erysipeloid, septicemia and pyoderma caused by hemolytic *Streptococci*; pulmonary tuberculosis, joint tuberculosis, renal tuberculosis and tuberculous meningitis caused by *Mycobacterium tuberculosis*; or bacterial gastroenteritis caused by *Salmonella* and *Vibrio parahaemolyticus*. In addition, the infectious disease caused by pathogenic yeast and fungi may be cryptococcosis, candidasis, dermatophytosis, superficial mycoses, meningitis, brain abscess, brain tumor, histoplasmosis, *pneumocystis* pneumonia or aspergillosis.

As used herein, the term "treatment" refers to all actions that restore or beneficially change the infection caused by pathogenic bacteria, yeast or fungi by administering the antimicrobial pharmaceutical composition. As used herein, the term "subject" refers to all animals, including humans, who have or are at risk of developing the infectious disease caused by pathogenic bacteria, yeast or fungi.

The antimicrobial pharmaceutical composition of the present invention can be administered to a human subject suffering from an infectious disease caused by pathogenic bacteria, yeast or fungi in order to treat the infectious disease.

The antimicrobial pharmaceutical composition of the present invention may be administered by any general route, as long as it can reach a target tissue. Specifically, the pharmaceutical composition of the present invention may be administered intraperitoneally, intravenously, intramuscularly, subcutaneously, intradermally, orally, intranasally, intrapulmonarily or intrarectally, but is not limited thereto. In addition, the pharmaceutical composition may be administered using any system capable of delivering the active ingredient to a target cell.

When the antimicrobial pharmaceutical composition comprising the antimicrobial microorganism of the present invention is administered in vivo, the multimeric antimicrobial peptide complex displayed on the cell surface of the antimicrobial microorganism is digested by the digestive enzyme pepsin in vivo and separated into monomeric antimicrobial peptide units having antimicrobial activity, indicating that the process of isolating and purifying the antimicrobial peptide is not required. In addition, the antimicrobial peptide cleaved into monomeric units by pepsin has high antimicrobial activity, and thus can be effectively used to eliminate pathogens.

In the Example of the present invention, an *E. coli* strain that displays the multimeric antimicrobial peptide complex on the cell surface thereof was treated with pepsin, and then the antimicrobial activity of the monomeric antimicrobial peptide units separated by pepsin was measured. As a result, it could be seen that the monomeric antimicrobial peptide had high antimicrobial activity against gram-positive *Staphylococus aureus*, gram-negative *Escherichia coli* and yeast *Saccharomyces cerevisiae* (Example 6 and FIG. 7).

The antimicrobial pharmaceutical composition of the present invention may include pharmaceutically acceptable carriers. The antimicrobial pharmaceutical composition may be in the form of various oral or parenteral formulations. The antimicrobial pharmaceutical composition is formulated using conventional diluents or excipients, including fillers, extenders, binders, wetting agents, disintegrants, and surfactants. Solid formulations for oral administration include tablets, pills, powders, granules, capsules, etc. These solid formulations may be prepared by mixing at least one compound with one or more excipients, for example, starch, calcium carbonate, sucrose, lactose, gelatin, etc. In addition, liquid formulations for oral administration include a suspension, a solution, an emulsion and a syrup, etc. In addition to water commonly used as a simple diluent and liquid paraffin, various excipients, for example, wetting agents, sweetening agents, flavors, preservatives, etc. may be included. Formulations for parenteral administration include sterilized aqueous solutions, non-aqueous solvents, suspending agents, emulsions, freeze-drying agents, suppositories, etc. Propylene glycol, polyethylene glycol, vegetable oils such as olive oil, injectable esters such as ethyl oleate, etc. may be used as non-aqueous solvents and suspending agents. Bases for suppositories may include witepsol, macrogol, tween 61, cacao butter, laurin butter, glycerinated gelatin, etc. In addition, the formulation may comprise nutrients required for displaying the multimeric antimicrobial peptide complex on the cell surface of the antimicrobial microorganism included in the antimicrobial pharmaceutical composition.

The antimicrobial pharmaceutical composition may have any one formulation selected from the group consisting of a tablet, a pill, powder, granules, a capsule, a suspension, a solution, an emulsion, a syrup, a sterilized aqueous solution, a non-aqueous solution, a suspension, an emulsion, a lyophilized formulation, and a suppository.

The pharmaceutical composition of the present invention may be administered in a pharmaceutically effective amount. As used herein, the term "pharmaceutically effective amount" refers to an amount sufficient to treat diseases, at a reasonable benefit/risk ratio applicable to any medical treatment. The effective dosage level of the composition may be determined depending on the subject's type, the disease severity, the subject's age and sex, the activity of the drug, sensitivity to the drug, the time of administration, the route of administration, excretion rate, the duration of treatment, drugs used in combination with the composition, and other factors known in the medical field. The pharmaceutical composition of the present invention may be administered alone or in combination with other therapeutic agents, and may be administered sequentially or simultaneously with conventional therapeutic agents. The composition can be administered in a single or multiple dosage form. It important to administer the composition in the minimum amount that can exhibit the maximum effect without causing side effects, in view of all the above-described factors.

In order to treat, an infectious disease caused by pathogenic bacteria, yeast or fungi, the pharmaceutical composition of the present invention may be used alone or in combination with surgery, hormonal therapy, drug therapy and a biological reaction regulator.

In still another aspect, the present invention provides an antimicrobial over-the-counter (OTC) drug composition comprising the inventive antimicrobial microorganism as an active ingredient. In other words, the present invention provides an OTC drug composition for preventing or ameliorating an infectious disease caused by pathogenic bacteria, yeast or fungi.

In the present invention, the OTC drug composition may be used together with other OTC drugs or OTC drug components and can be appropriately used according to conventional methods. The amount of active ingredient added can be suitably determined according to the intended use (prophylactic or therapeutic treatment).

The OTC drug composition may be in the form of a disinfectant, shower foam, a mouth wash, a wet tissue, a detergent soap, a hand wash, a filler for humidifiers, a facial mask, an ointment or a filler for filters.

In still another aspect, the present invention provides a method for preparing an antimicrobial composition that displays the multimeric antimicrobial peptide complex of the present invention on the cell surface thereof.

The preparation method according to the present invention comprises the steps of: (a) preparing a recombinant vector comprising a polynucleotide encoding the multimeric antimicrobial peptide complex of the present invention; (b) introducing the recombinant vector into a host cell to obtain a transformant; and (c) culturing the transformant to induce the expression of the multimeric antimicrobial peptide complex.

The step of transforming the host cell by introducing the recombinant vector comprising the DNA of the present invention may be performed using any method known in the art. Examples of the transformation method include, but are not limited to, transient transfection, microinjection, transduction, cell fusion, calcium phosphate precipitation, liposome-mediated transfection, DEAE dextran-mediated transfection, polybrene-mediated transfection, electroporation and the like.

The step of culturing the transformant to induce the expression of the multimeric antimicrobial peptide complex may be performed using any method known in the art. For example, the expression of the multimeric antimicrobial peptide complex can be induced by IPTG in LB medium at 37° C. under aerobic conditions, which are general conditions for the growth of *E. coli* cells.

Figure 6:
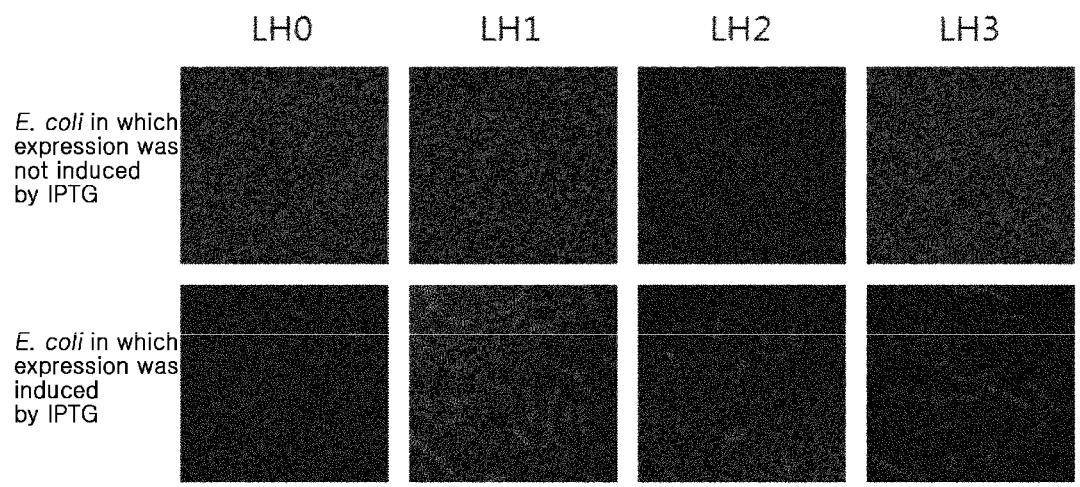
FIG. 6 is a confocal micrograph showing a multimeric microbial peptide displayed on the cell surface of transformed E. coli. "M" in FIG. 5 represents a molecular weight standard marker; LH0 in FIGS. 5 and 6 indicates the IPTG-induced expression of a cell surface anchoring motif alone, and the arrow in LH1, LH2 and LH3 indicates the IPTG-induced expression of the monomer, dimer and trimer of the antimicrobial peptide Hinge2L linked to the cell surface anchoring motif.

In one Example of the present invention, *E. coli* BL21 (DE3) was transformed with each of the recombinant vectors pLH0, pLH1, pLH2 and pLH3 using a CaCl$_2$-based transformation method in order to express the multimeric antimicrobial peptide complex of the present invention (Example 4). As can be seen in FIG. 6, the multimeric antimicrobial peptide complex was displayed on the cell surface of the *E. coli* strains transformed with the recombinant vectors (FIG. 6).

The antimicrobial microorganism produced by the method of the present invention displays the pepsin-digested multimeric antimicrobial peptide complex on the cell surface thereof. Thus, when the antimicrobial microorganism is administered in vivo in a living state, the multimeric antimicrobial peptide complex will be separated into monomeric antimicrobial peptide units having antimicrobial activity by pepsin, indicating that the process of lysing the microbial cell and isolating and purifying the antimicrobial peptide is not required. In addition, the separated antimicrobial peptide units exhibits high antimicrobial activity, and thus can be effectively used to eliminate pathogens.

MODE FOR INVENTION

Hereinafter, the present invention will be described in further detail with reference to examples and test examples. It is to be understood, however, that these examples are for illustrative purposes only and are not intended to limit the scope of the present invention.

Example 1: Determination of Sequence of Amino Acid Linker that is Digested by Pepsin and Measurement of Antimicrobial Activity of Monomeric Antimicrobial Peptide Comprising the Amino Acid Linker 1-1: Determination of Sequence of Amino Acid Linker that is Digested by Pepsin In order to prepare an antimicrobial peptide polymer which is separated into monomeric units by pepsin, antimicrobial peptide units (SEQ ID NO. 9: RVVRQWPIGRV-VRRVVRRVVR) of SEQ ID NO: 1 disclosed in Korean Patent Registration No. 0441402 were linked to each other using any amino acid as a linker, thereby obtaining an antimicrobial peptide polymer. Then, the sequence of the amino acid linker that is digested by pepsin to separate the peptide polymer into monomeric forms was determined using the computer program tool ExPAsy (Expert protein analysis system, Swiss). As a result, a peptide linkage formed between the C-terminus of each of leucine, phenylalanine and tyrosine and the N-terminus of the antimicrobial peptide was digested by pepsin, and each of the amino acids was determined to be an amino acid linker that is digested by pepsin.

1-2: Measurement of Antimicrobial Activity of Monomeric Antimicrobial Peptide Having Amino Acid Linker that is Digested by Pepsin Added Thereto The amino acid sequence of the antimicrobial peptide polymer obtained by adding the amino acid linker, which is digested by pepsin, to the antimicrobial peptide, was predicted using a program, and as a result, it was shown that pepsin acted downstream of leucine, phenylalanine and tyrosine. Based on this finding, for these three peptides, 95% pure antimicrobial peptides were obtained by chemical synthesis.

The antimicrobial activities of the prepared antimicrobial peptides against microorganisms were measured by a 96-well microdilution minimal inhibitory concentration assay. Specifically, bacteria and fungi were cultured overnight in trypticase soy broth (TSB) at 37° C. and 30° C., respectively, and then the cells were inoculated in fresh media and cultured for 2 hours to the exponential growth phase. Then, the cells were diluted to a density of $10^5$ cells/ml, and 10 μl of the dilution was seeded into each well of a 96-well plate, after which each well was treated with 10 μl of the serially diluted antimicrobial peptides. The 96-well plate was incubated for 12 hours, and the absorbance of each well was measured. Herein, the minimum concentration at which the microbial cells could not grow was determined as the minimum inhibitory concentration. The results of the measurement are shown in Table 1 below. In Table 1, Hinge2L, Hinge2F and Hinge2Y indicate the antimicrobial peptides obtained by adding leucine, phenylalanine and tyrosine to the antimicrobial peptide of SEQ ID NO: 9, respectively.

TABLE 1

|  | Hinge2L | Hinge2F | Hinge2Y |
|---|---|---|---|
| *Staphylococus. aureus* (G+) | 2 μl | 4 μl | 8 μl |
| *Escherichia. coli* (G−) | 2 μl | 4 μl | 8 μl |
| *Saccharomyces. serevisiae* (Yeast) | 2 μl | 4 μl | 8 μl |

As can be seen from the results in Table 1 above, the peptide comprising leucine added to the antimicrobial peptide had the highest antimicrobial activity of 2 μl/ml against gram-positive *Staphylococus aureus*, gram-negative *Escherichia coli*, and yeast *Saccharomyces cerevisiae* (Table 1).

Example 2: Preparation of Antimicrobial Peptide Polymer which is Digested by Pepsin A DNA fragment was constructed, which encodes the monomeric antimicrobial peptide (Hinge2L) comprising the amino acid linker (leucine) that is digested by pepsin added to the C-terminus of the antimicrobial peptide as described in Example 1. The DNA vector was cloned into a vector. Specifically, PCR was performed using primers of SEQ ID NO: 1 (5'-GAAGACCCCGTGTTGTTCG TCAGTGGC-CGATTGGTCGTGTCGTTCGCCGTGTTGTTCG-3') and SEQ ID NO: 2 (5'-GGATGGATCCTAAGCACGCAGAC-GAACGACGCGACGAACAACACGGCGAACGA-CACG-3'), thereby obtaining a double-stranded DNA fragment encoding a monomeric antimicrobial peptide (consisting of 22 amino acids) comprising the amino acid linker that is digested by pepsin leucine added to the C-terminus of the antimicrobial peptide of SEQ ID NO: 9. The PCR reaction was performed for 30 cycles, each consisting of DNA denaturation at 94° C. for 30 sec, annealing at 56° C. for 30 sec and DNA synthesis at 72° C. for 30 sec. For cloning, the restriction enzyme BbsI recognition site (5'-GAAGAC(N)$_2$▼-3', 3'-CTTCTG(N)$_6$▲-5') was introduced into the N-terminus of the monomeric antimicrobial peptide, and the FokI recognition site (5'-GGATG(N)$_9$▼-3', 3'-CCTAC(N)$_{13}$▲-5') was introduced into the C-terminus.

Then, the obtained DNA fragment was inserted into a pGEM T-easy vector, and the resulting vector was named "pMBT-H".

Figure 2:
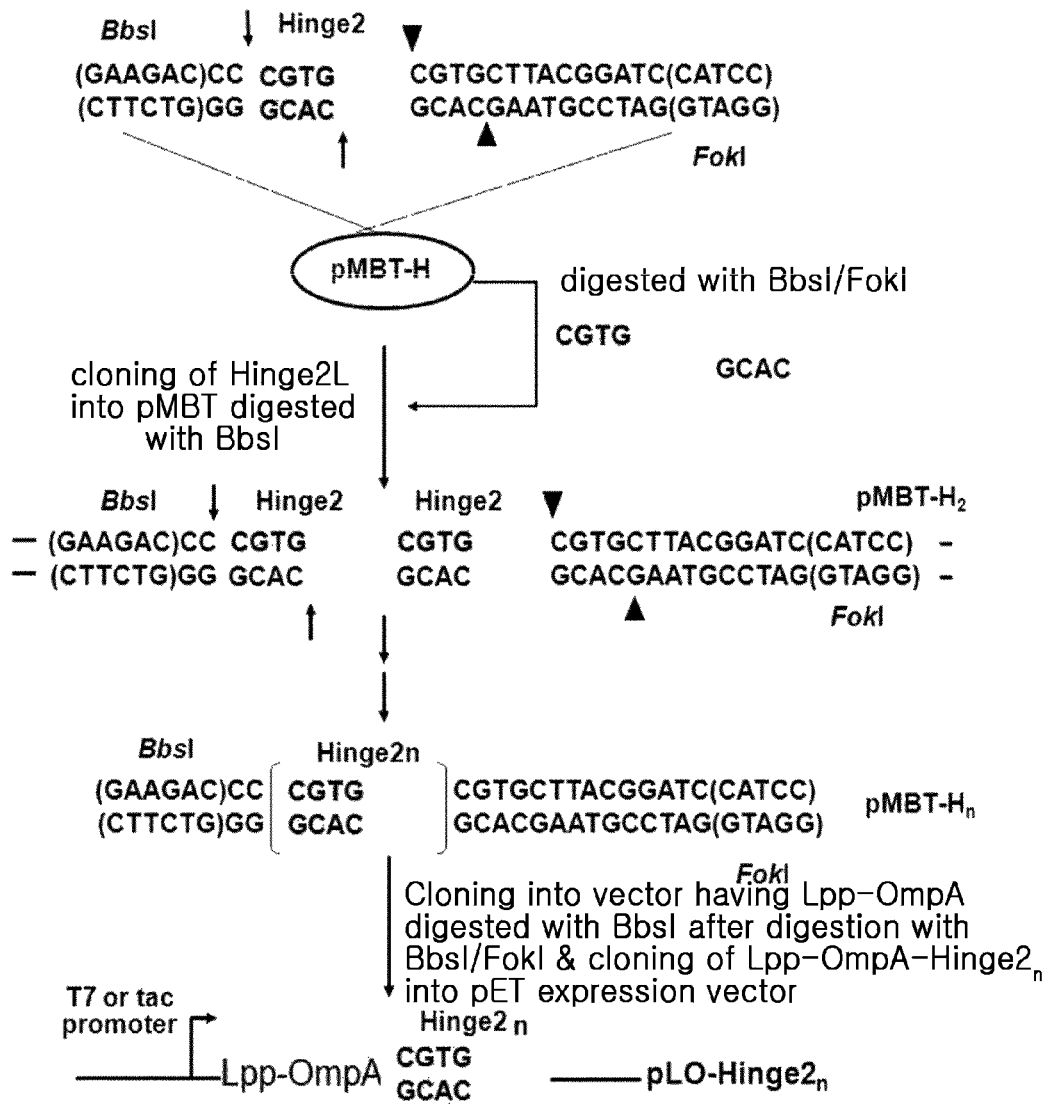
FIG. 2 schematically shows a process for constructing the inventive multimeric antimicrobial peptide complex that is displayed on the cell surface.

In addition, in order to construct an antimicrobial peptide polymer, the DNA fragment encoding the monomeric antimicrobial peptide Hinge2L, constructed by PCR, was digested with the restriction enzymes BbsI and FokI, and then inserted into a pMBT-H vector digested with the restriction enzyme BbsI, thereby constructing a pMBT-H$_2$ vector comprising two Hinge2L units linked thereto. In an identical process, pMBT-H$_3$, pMBT-H$_4$ . . . pMBT-H$_n$ were constructed (FIG. 2).

Example 3: Construction and Cloning of DNA Fragment of Antimicrobial Peptide Polymer Linked to Cell Surface Anchoring Motif 3-1: Construction and Cloning of Antimicrobial Peptide Polymer DNA Linked to Lpp-OmpA In order for the antimicrobial peptide polymer to be displayed on the host cell surface, a Lpp-OmpA DNA fragment serving as a cell surface anchoring motif was constructed, which has the nucleotide sequence of SEQ ID NO: 7 comprising a portion of an *E. coli* outer membrane protein A (OmpA) attached to the leader sequence of *E. coli* lipoprotein and to the cell outer membrane. The Lpp-OmpA DNA fragment was cloned into a vector.

Specifically, in order to construct the Lpp-OmpA DNA fragment, primers of SEQ ID NO: 3 (5'-CGCCATAT-GAAAGCTACTAAACTGG TACTGGGCAACAACAATGGCCCGACC-3'), SEQ ID NO: 4 (5'-GCAAACACCGGAGAAAC GCCGGTG-3'), SEQ ID NO: 5 (5'-TTCTCCGGTGTTTGCTGGCGGT-GTTG-3') and SEQ ID NO: 6 (5'-CGGGATCCTAGT-GATGGTGATGGTGATGAACACGCAGTCT TCCACGGGTAG-3') were synthesized, recombinant PCR was performed using the genomic DNA of *E. coli* MG1655 as a template and the synthesized primers for 30 cycles, each consisting of DNA denaturation at 94° C. for 30 sec, annealing at 54° C. for 30 sec and DNA synthesis at 72° C. for 90 sec, thereby obtaining a DNA fragment (369 nucleotides) encoding a Lpp-OmpA polypeptide consisting of 123 amino acids.

Then, in order to achieve effective cloning while preventing a change in amino acids from occurring during expression, C at position 321 of the restriction enzyme BbsI recognition site of the Lpp-OmpA DNA sequence obtained by the recombinant PCR method was replaced with G, and C at position 324 was replaced with T, thereby constructing a Lpp-OmpA DNA fragment (SEQ ID NO: 7). In order to clone the constructed Lpp-OmpA DNA fragment into a vector, the restriction enzyme NdeI recognition site (CATATG) was introduced into the N-terminus of Lpp-OmpA, and the restriction enzyme BbsI recognition site (5'-GAAGAC(N)$_2$ ▼-3', 3'-CTTCTG(N)$_6$▲-5') was inserted into the C-terminus so that the antimicrobial peptide polymer DNA fragment constructed in Example 2 could be linked, and the restriction enzyme BamHI recognition site (GGATCC) was also introduced into the C-terminus. In addition, His tag was introduced in order to confirm expression.

The obtained DNA fragment was inserted into a pGEM T-easy vector, and the resulting vector was named "pLO vector". The pLO vector was digested with BbsI, and pMBT-Hn constructed in Example 2 was digested with the restriction enzymes BbsI and FokI to obtain the DNA fragment of the antimicrobial peptide polymer Hinge2Ln, which was then ligated with the pLO vector digested with the restriction enzyme, thereby constructing pLO-Hinge2Ln vectors (n indicates the number of monomeric antimicrobial peptide Hinge2L units; FIG. 2) including the DNA fragment (Lpp-OmpA-Hinge2Ln) consisting of the antimicrobial peptide polymer DNA linked to Lpp-OmpA.

3-2: Measurement of Size of Lpp-OmpA-Hinge2Ln DNA Fragment

In order to confirm whether the DNA fragment was cloned, the size of the Lpp-OmpA-Hinge2Ln DNA fragment inserted in the pLO-Hinge2Ln vector constructed in Example 3-1 was measured.

Figure 3:
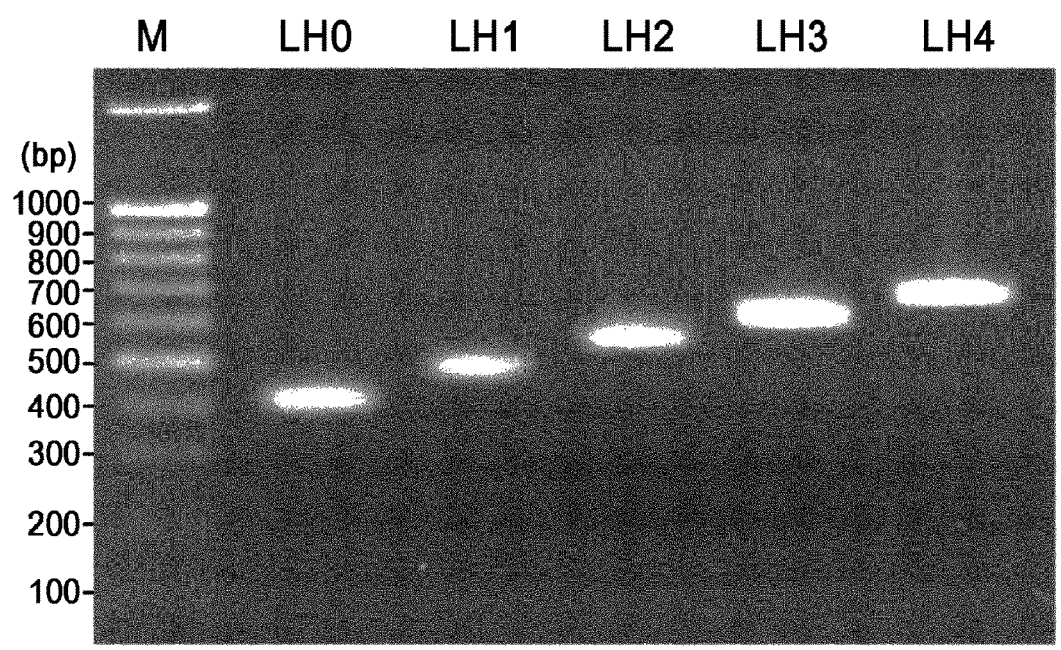
FIG. 3 is an agarose gel image showing the size of a Lpp-OmpA-Hinge2Ln DNA fragment.

Specifically, each of the pLO-Hinge2Ln vectors was treated with the restriction enzyme NotI, and the size of the Lpp-OmpA-Hinge2Ln DNA fragment inserted into each vector was measured. The results of the measurement are shown in FIG. 3. For electrophoresis, 0.3 g of 1% agarose gel was added to 30 ml of 1×TBE (Tris, Boric acid, EDTA) buffer and boiled in a microwave oven. The solution was poured into a mold and allowed to stand for 30 minutes so as to be hardened. Then, 10 μl of a Lpp-OmpA-Hinge2Ln DNA solution was added to 2 μl of 6× loading dye, loaded onto the gel, and electrophoresed at 100 V for 40 minutes. Then, the gel was stained in EtBr solution for 20 minutes and washed with water for 15 minutes.

FIG. 3 is an electrophoresis image showing the sizes of the Lpp-OmpA-Hinge2Ln DNA fragments. In FIG. 3, M represents a DNA size marker, and lanes LH0, LH1, LH2, LH3 and LH4 represent the size of the Lpp-OmpA-Hinge2Ln DNA fragments. Specifically, LH0 represents Lpp-OmpA, and LH1, LH2, LH3 and LH4 presents the numbers of monomeric antimicrobial peptide units linked to the cell surface anchoring motif Lpp-OmpA, respectively.

As can be seen in FIG. 3, the multimeric antimicrobial peptide complex (Lpp-OmpA-Hinge2Ln DNA) comprising the antimicrobial peptide polymer linked to the cell surface anchoring motif Lpp-OmpA was effectively cloned into the vector (FIG. 3).

Figure 4:
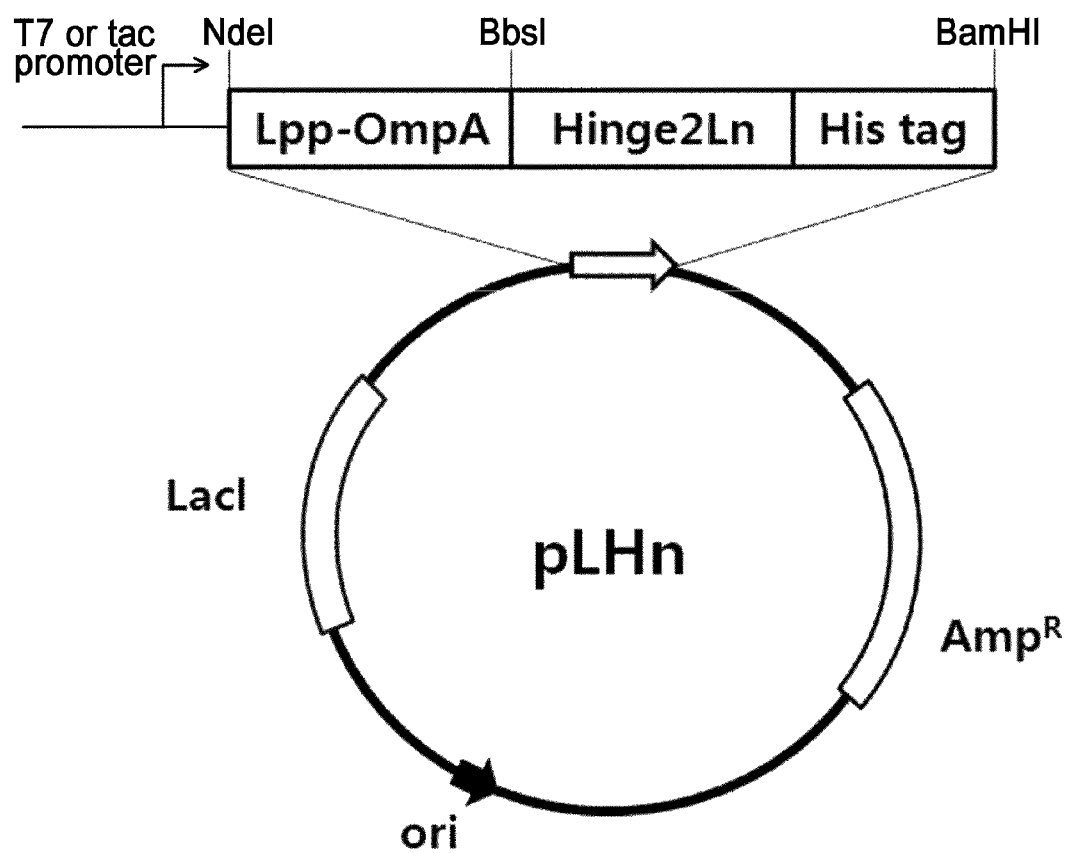
FIG. 4 is a schematic view of the recombinant vector pLHn including the Lpp-OmpA-Hinge2Ln DNA fragment inserted therein.

Example 4: Construction of Microorganism Displaying Multimeric Antimicrobial Peptide Complex (Lpp-OmpA-Hinge2Ln) on Cell Surface As shown in FIG. 4, the multimeric antimicrobial peptide complex and a His tag were linked to Lpp-OmpA DNA, thereby constructing recombinant vectors. Specifically, each of the pLO-Hinge2Ln vectors constructed in Example 3 was treated with the restriction enzymes NdeI and BamHI to obtain Lpp-OmpA-Hinge2Ln DNA fragments, and DNA fragments having desired sizes were separated therefrom using a gel extraction kit (Qiagen, Germany).

Each of the separated DNA fragments was linked to a pET21c vector digested with NdeI and BamHI, thereby constructing pLHn (pLH0, pLH1, pLH2 . . . , n=number of Hinge2L monomers) vectors (FIG. 4). Then, each of the pLH0, pLH1, pLH2 and pLH3 vectors was introduced into *E. coli* BL21 (DE3) by a CaCl$_2$-based transformation method.

Example 5: Examination of Whether Multimeric Antimicrobial Peptide Complex (Lpp-OmpA-Hinge2Ln) was Displayed on Cell Surface Whether the multimeric antimicrobial peptide complex was displayed on the cell surface of the transformed *E. coli* strain of the Example 4 was examined. Specifically, the transformed *E. coli* cells were cultured in LB medium (Luria Botani, 1% tryptone, 0.5% yeast extract, and 0.5% NaCl), and when the culture medium reached an OD$_{600}$ of 0.5-0.6, 0.2 mM IPTG (isopropyl-β-D-thiogalactopyranoside was added thereto to induce the expression of the multimeric antimicrobial peptide complex on the cell surface. 4 hours after the induction of the expression, the medium was removed, and the cells were washed twice with PBS (phosphate buffered saline), and 0.2% BSA (bovine serum albumin)-containing PBS and His-tag primary antibody were to the cells which were then incubated on ice for 30 minutes. After the incubation, the cells were washed twice with PBS, and FITC conjugated His tag secondary antibody was added to the cells which were then incubated on ice for 30 minutes under light-shielded conditions. Then, the *E. coli* cells were washed with PBS, resuspended in PBS, and observed with a confocal microscope.

Figure 5:
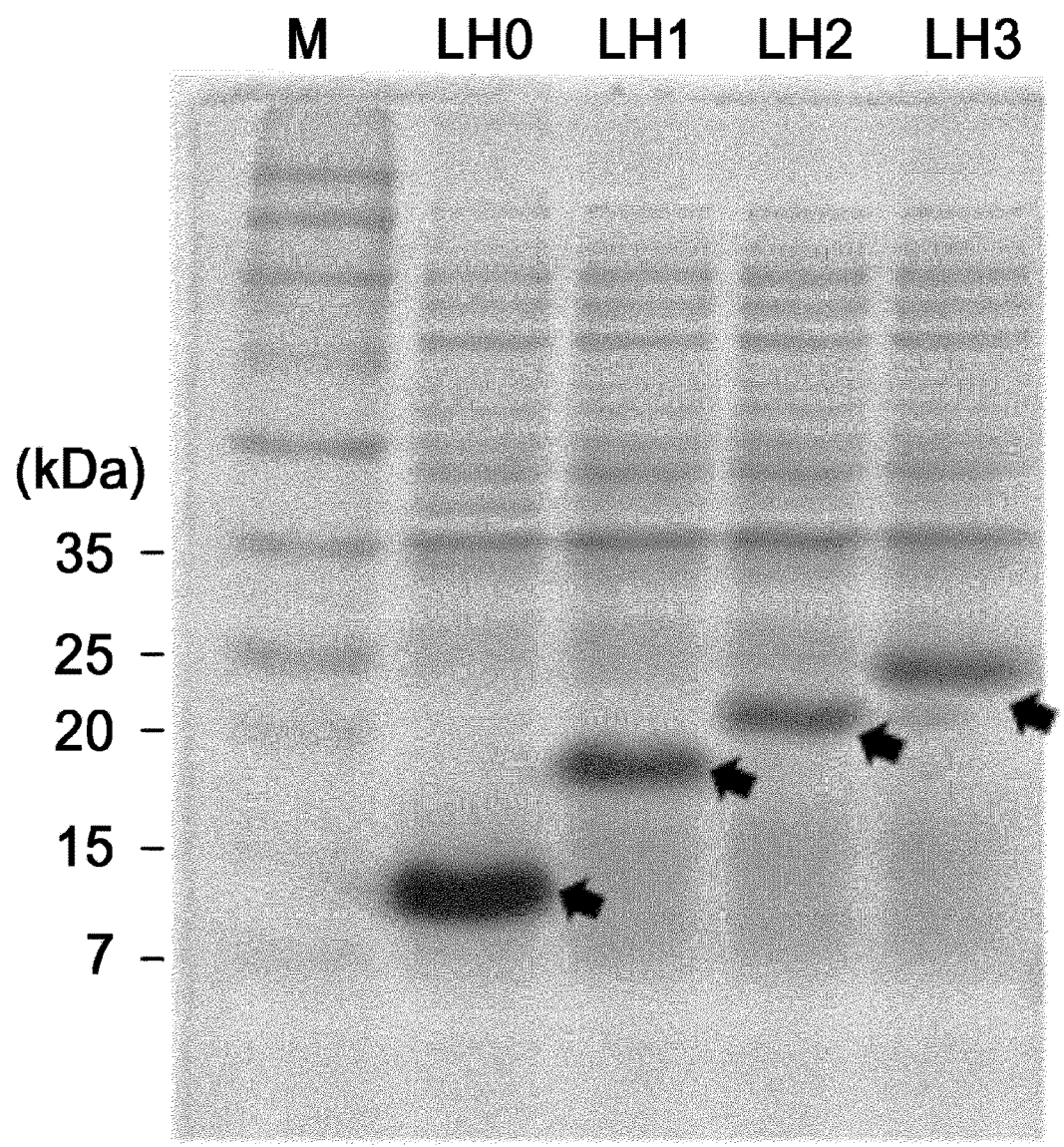
FIG. 5 is a SDS-PAGE image showing the size of the Lpp-OmpA-Hinge2Ln DNA fragment displayed on transformed E. coli.

As a result, it was shown that the expression of the cell surface anchoring motif which was not linked to the monomeric antimicrobial peptide was induced by IPTG (LH0), and the expressions of cell surface anchoring motif-monomeric antimicrobial peptide, cell surface anchoring motif-dimeric peptide, and cell surface anchoring motif-trimeric peptide were induced by IPTG (FIG. 5).

In addition, it could be seen that the multimeric antimicrobial peptide complexes LH1, LH2 and LH3 linked to the cell surface anchoring motif were displayed on the cell surface of the transformed E. coli by IPTG (FIG. 6).

Example 6: Examination of Antimicrobial Activity of Multimeric Antimicrobial Peptide Complex Displayed on Cell Surface The antimicrobial effect of the E. coli strain, constructed in Example 4 and displaying the multimeric antimicrobial peptide complex on the cell surface, was measured. Specifically, the transformed E. coli BL21 (DE3) was cultured in 100 ml of LB medium, and when the culture medium reached an $OD_{600}$ of 0.5-0.6, 0.2 mM IPTG was added thereto to induce the expression of the multimeric antimicrobial peptide complex linked to the cell surface anchoring motif. 4 hours after the induction of the expression, the medium was removed, and the cells were washed twice with NAPB (sodium phosphate buffer), and then resuspended in the same buffer. All the E. coli samples were adjusted to a cell number of $1\times10^{10}$ cfu/ml. Then, pepsin was dissolved in simulated gastric fluid (SGF) (0.084 N HCl, 35 mM NaCl, pH 1.2 or 2.0), and the E. coli cells were treated with the pepsin solution and incubated for 30 minutes. After the incubation, in order to deactivate pepsin and neutralize the pH, the same concentration of NaOH aqueous solution as that of the simulated gastric fluid was added to the cells, and the cell solution was centrifuged to remove cell debris other than the monomeric antimicrobial peptide digested by pepsin.

The antimicrobial activities of the pepsin-digested monomeric antimicrobial peptide against gram-positive Staphylococus aureus, gram-negative Escherichia coli and the yeast Saccharomyces cerevisiae were measured.

Each of the microbial strains was collected in the exponential growth phase during the culture, washed twice with NAPB, and then resuspended in the same buffer. The number of the microbial cells was adjusted to $1\times10^5$ cfu/ml. 10 μl of an aqueous solution containing each microbial strain and the pepsin-digested monomeric antimicrobial peptide was dispensed into each well of a 96-well plate, mixed well and incubated at 37° C. for 3 hours. After 3 hours, 2×TSB (Trypticase Soy Broth) medium was added to the cells which were then incubated at 37° C. for 12 hours, after which the absorbance at $OD_{595}$ was measured.

Figure 7:
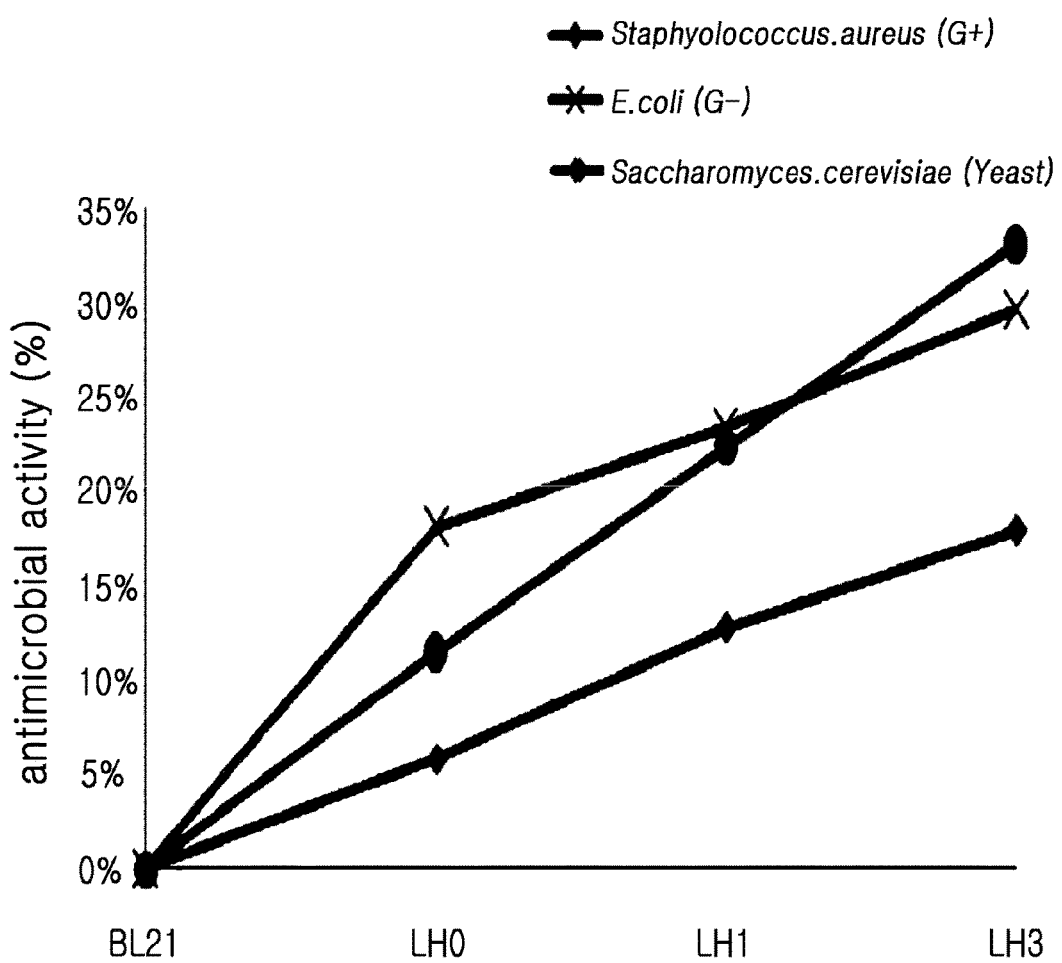
FIG. 7 is a graphic diagram showing the antimicrobial activity of an E. coli strain expressing a multimeric antimicrobial peptide complex and shows the results of observation of the antimicrobial activities of the monomeric antimicrobial peptides LH0, LH1 and LH3 cleaved by pepsin, when the activity of E. coli BL21 (DE3) as a negative control, which does not express the antimicrobial peptide, was defined as 0%, and the activity of the synthesized monomeric antimicrobial peptide Hinge2L as a positive control was defined as 100%.

As a result, among the multimeric antimicrobial peptide complexes, LH3 showed antimicrobial activities of 17.95% against gram-positive Staphylococus aureus, 30% against gram-negative Escherichia coli, and 33.17% against yeast Saccharomyces cerevisiae, indicating that LH3 showed the highest antimicrobial activity (FIG. 7). Such results suggest that the antimicrobial activity of the multimeric antimicrobial peptide complex increases as the number of monomeric antimicrobial peptide units therein increases, and when antimicrobial microorganisms displaying this multimeric antimicrobial peptide complex are administered in vivo, they can show antimicrobial effects, including the elimination of pathogens and the activation of immune cells. Thus, it can be seen that the antimicrobial peptide can be used without having to isolate and purify the antimicrobial peptide, suggesting that the antimicrobial peptide can have widespread use.

---

The invention claimed is:

1. A method for producing an antimicrobial transformant displaying a multimeric antimicrobial peptide complex on the cell surface thereof, comprising
    (a) preparing a recombinant vector comprising a polynucleotide encoding the multimeric antimicrobial peptide complex comprising a cell surface anchoring motif linked to the antimicrobial peptide via an amino acid linker, wherein the complex is represented by the following formula 1 or 2:
        (1) a cell surface anchoring motif—[an amino acid linker that can be digested randomly by pepsin—an antimicrobial peptide]$_n$,
        (2) a cell surface anchoring motif—[an antimicrobial peptide—an amino acid linker that can be digested randomly by pepsin]$_n$,
    wherein n is an integer greater than 1; and
    wherein the antimicrobial peptide does not comprise leucine, phenylalanine, and tyrosine;
    both amino acid terminuses of the linker are an amino acid selected from the group consisting of leucine, phenylalanine and tyrosine;
    the peptide linkage formed between the end of the linker and the terminus of the antimicrobial peptide, and the peptide linkage formed between the end of the linker and the terminus of the cell surface anchoring motif can be cleaved by the action of the extracellular digestive enzyme pepsin; and
    the cell surface anchoring motif is selected from the group consisting of outer membrane proteins, lipoproteins, autotransporters, and S-layer of a surface appendage;
    (b) introducing the recombinant vector into a host cell to obtain a transformant; and
    (c) culturing the transformant to induce the expression of the multimeric antimicrobial peptide complex, wherein the expressed multimeric antimicrobial peptide complex is displayed and anchored to the surface of the antimicrobial transformant.

2. The method for producing the antimicrobial transformant of claim 1, wherein the antimicrobial peptide has any one of amino acid sequences represented by SEQ ID NOS: 9 to 24.

3. The method for producing the antimicrobial transformant of claim 1, wherein the cell surface anchoring motif is linked to the N-terminus of the polymer.

4. The method for producing the antimicrobial transformant of claim 1, wherein the cell surface anchoring motif is an outer membrane protein.

5. The method for producing the antimicrobial transformant of claim 4, wherein the outer membrane protein is selected from the group consisting of an *E. coli* outer membrane protein OmpA, an *E. coli* outer membrane protein OmpA linked to the leader sequence of *E. coli* lipoprotein, an *E. coli* outer membrane protein OmpS, an *E. coli* outer membrane protein LamB, an *E. coli* outer membrane protein PhoE, an *E. coli* outer membrane protein OmpC, an *E. coli* outer membrane protein FadL, a *Salmonella* outer membrane protein OmpC, and a *Pseudomonas* outer membrane protein OprF.

6. The method for producing the antimicrobial transformant of claim 1, wherein the cell surface anchoring motif is an *E. coli* outer membrane protein OmpA linked to the leader sequence of *E. coli* lipoprotein which comprises the sequence of SEQ ID NO: 8.

7. The method for producing the antimicrobial transformant of claim 1, wherein the antimicrobial peptide comprises the sequence of SEQ ID NO: 9, the amino acid linker digested by pepsin is leucine, and the cell surface anchoring motif comprises the sequence of SEQ ID NO: 8.

* * * * *